United States Patent [19]

Hodgson

[11] 3,997,970
[45] Dec. 21, 1976

[54] ORTHODONTIC OCCLUSION-IMPROVING APPLIANCE

[76] Inventor: Edward W. Hodgson, 3006 Pershall, St. Louis, Mo. 63136

[22] Filed: Oct. 6, 1975

[21] Appl. No.: 619,605

[52] U.S. Cl. .............................. 32/14 R; 32/14 E
[51] Int. Cl.² .................................... A61C 7/00
[58] Field of Search ............... 32/14 A, 14 R, 14 E

[56] References Cited

UNITED STATES PATENTS

| 3,618,214 | 11/1971 | Armstrong | 32/14 A |
| 3,654,702 | 4/1972 | Kelly, Jr. | 32/14 A |
| 3,878,609 | 4/1975 | Wallshein | 32/14 A |

FOREIGN PATENTS OR APPLICATIONS

| 2,239,807 | 3/1973 | Germany | 32/14 A |
| 335,395 | 2/1936 | Italy | 32/14 A |

OTHER PUBLICATIONS

"Patents of Interest", *Straight Talk*, TP Labs, Indiana, Mar. 1972.
"SAIF Springs Improved Version of 'Pace Multicoils'", *Straight Talk*, TP Labs, Indiana, May 1972.
"Patents of Interest", *Straight Talk*, TP Labs, Indiana, Mar. 1973.

*Primary Examiner*—Louis G. Mancene
*Assistant Examiner*—Jack O. Lever
*Attorney, Agent, or Firm*—Rogers, Eilers & Howell

[57] ABSTRACT

A helical extension spring is telescoped over, and is supported and guided by, an orthodontic arch wire which is secured to one jaw of a person; and a flexible connector extends between one end of that helical extension spring and the other jaw of that person. The helical extension spring permits the jaws to open and close; but it continuously applies a repositioning force to those jaws which tends to improve the occlusion of those jaws.

14 Claims, 8 Drawing Figures

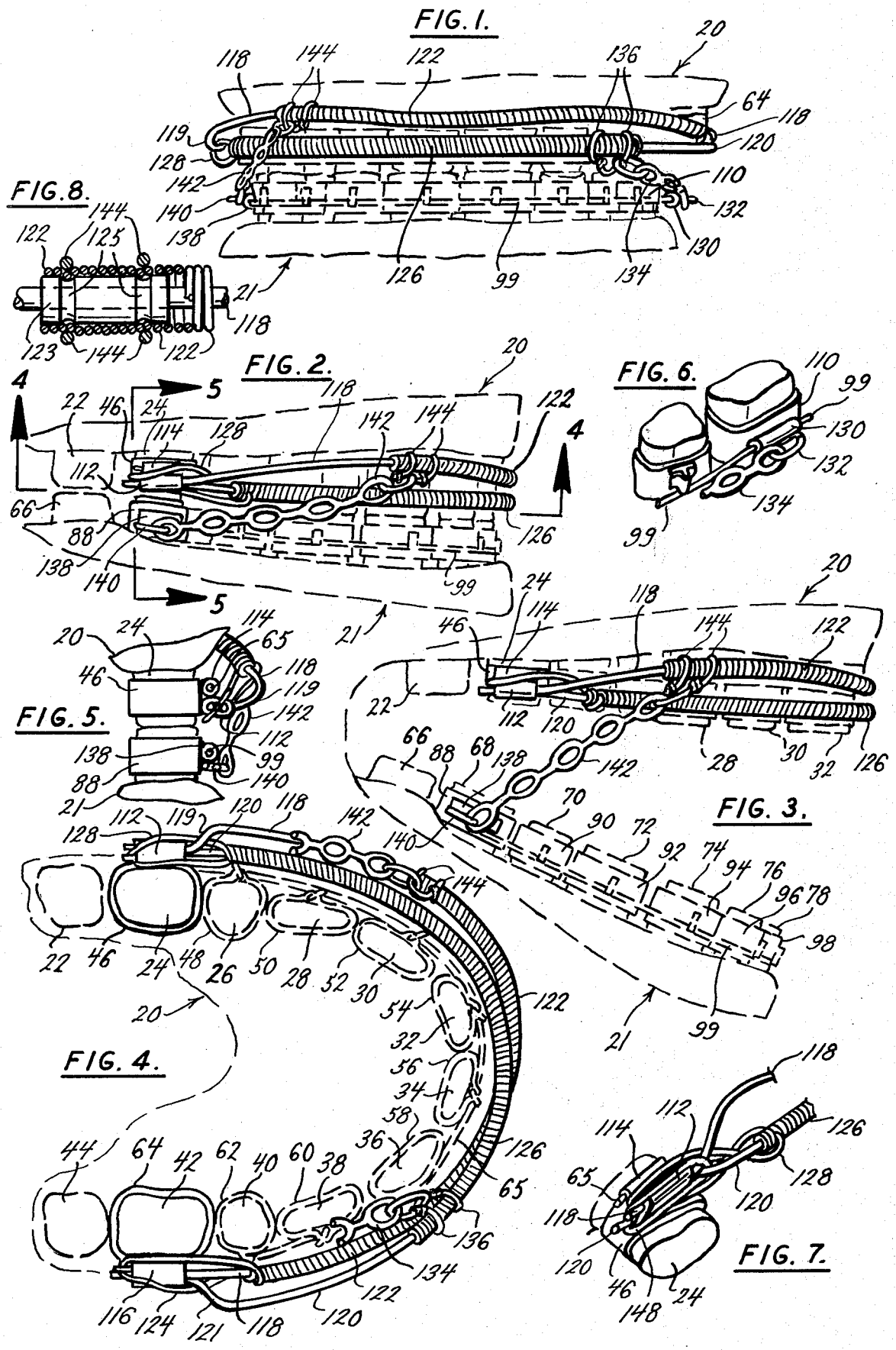

ORTHODONTIC OCCLUSION-IMPROVING APPLIANCE

BACKGROUND OF THE INVENTION

The upper and lower jaws of some persons do not directly register with each other, and hence mal-occlusion of those jaws can exist. In some instances the mal-occlusion of the jaws is of such a nature and of such an extent that the application of a yieldable force to those jaws over a prolonged period of time can eliminate the mal-occlusion. Some orthodontists have urged persons, who have correctable mal-occlusions, to attach rubber bands to hook-equipped metal orthodontic bands that are affixed to their teeth; because those rubber bands could supply repositioning forces which could reduce or eliminate the mal-occlusions. Unfortunately, rubber bands must be replaced several times a week or even daily; and many persons do not replace them. Other orthodontists have connected the ends of springs to the jaws of persons in an effort to reduce or eliminate mal-occlusions of those jaws; but the repositioning forces applied by those springs frequently were too large, and portions of those springs were occasionally bitten by the teeth of those persons.

SUMMARY OF THE INVENTION

The present invention provides a helical extension spring which is telescoped over, and which is supported and guided by an orthodontic arch wire that is secured to teeth on one jaw of a person and also provides a flexible connector which extends between one end of that helical extension spring and a tooth on the other jaw of that person. That helical extension spring and that flexible connector do not require periodic replacement, that helical extension spring provides a gentle repositioning force, and that orthodontic arch wire keeps that helical extension spring from being bitten by the teeth of that person. It is, therefore, an object of the present invention to provide a helical extension spring which is telescoped over, and which is supported and guided by, an orthodontic arch wire that is secured to teeth on one jaw of a person and also to provide a flexible connector which extends between one end of that helical extension spring and a tooth on the other jaw of that person.

The orthodontic arch wire is disposed outwardly of the outer faces of the teeth on the one jaw of the person, and hence tends to keep the flexible connector from getting into the space between the teeth of that person. However, even if that flexible connector does get between the teeth of that person, it will not cause breaking or chipping of any of those teeth, and it will not be severed by those teeth, because it is made of a tough non-metallic material. It is, therefore, an object of the present invention to provide a helical extension spring which is telescoped over, and which is supported and guided by, an orthodontic arch wire that is secured to teeth on one jaw of a person and also to provide a tough, non-metallic, flexible connector which extends between one end of that helical extension spring and a tooth on the other jaw of that person.

Other and further objects and advantages of the present invention should become apparent from an examination of the drawing and accompanying description.

In the drawing and accompanying description a preferred embodiment of the present invention is shown and described but it is to be understood that the drawing and accompanying description are for the purpose of illustration only and do not limit the invention and that the invention will be defined by the appended claims.

BRIEF DESCRIPTION OF THE DRAWING

In the drawing, FIG. 1 is a front elevational view of one embodiment of orthodontic occlusion-improving appliance which is made in accordance with the principles and teachings of the present invention as it appears when applied to the jaws of a person, FIG. 2 is a side elevational view of the orthodontic occlusion-improving appliance of FIG. 1, FIG. 3 is a side elevational view of the orthodontic occlusion-improving appliance of FIG. 1, but it shows the jaws of the person in open position, FIG. 4 is a bottom view of part of the orthodontic occlusion-improving appliance of FIG. 1 and of the upper jaw to which that part is attached, FIG. 5 is a side elevational view, on a larger scale, of part of the orthodontic occlusion-improving appliance of FIG. 1, and it is taken along the plane indicated by the line 5—5 in FIG. 2.

FIG. 6 is a perspective view, on a still larger scale, of the lower end of one of the flexible connectors of the orthodontic occlusion-improving appliance of FIG. 1, and it shows how that lower end is connected to the lower jaw, FIG. 7 is a perspective view, on the scale of FIG. 6, of one of the teeth of FIG. 5 and of the portions of the orthodontic occlusion-improving appliance of FIG. 1 that are connected to that tooth, and FIG. 8 is a sectional view, on a scale larger than that of FIG. 1, through one end of one of the helical extension springs of the orthodontic occlusion-improving appliance of FIG. 1.

DESCRIPTION OF THE PREFERRED EMBODIMENT

Referring to the drawing in detail, the numeral 20 generally denotes the upper jaw of a person, and the numeral 21 generally represents the lower jaw of that person. That upper jaw is shown as having six incisors 28, 30, 32, 34, 36 and 38, two bicuspids 26 and 40, and four molars 22, 24, 42 and 44. Because most persons have four bicuspids rather than two bicuspids, FIG. 4 represents an upper jaw from which two bicuspids have been extracted to provide room for relative movement of the remaining teeth. Orthodontic bands 46, 48, 50, 52, 54, 56, 58, 60, 62 and 64 of standard and usual design encircle, and are supported by, the teeth 24, 26, 28, 30, 32, 34, 36, 38, 40 and 42, respectively. Those orthodontic bands are intended to support an orthodontic arch wire 65 which is shown in dotted lines in FIG. 4 and which is intended to reposition one or more of the teeth 24, 26, 28, 30, 32, 34, 36, 38, 40 and 42. The manner of securing the orthodontic arch wire 65 to the orthodontic bands 46, 48, 50, 52, 54, 56, 58, 60, 62 and 64, and the manner in which that orthodontic arch wire will reposition one or more of the teeth 24, 26, 28, 30, 32, 34, 36, 38, 40 and 42, are well known to those skilled in the art and are not a part of the present invention.

The numerals 66, 68, 70, 72, 74, 76, and 78 represent some of the teeth in the lower jaw 21; and orthodontic bands 88, 90, 92, 94, 96 and 98 of standard and usual design are mounted on those teeth. Those orthodontic bands support an orthodontic arch wire 99 which is shown by dotted lines in FIGS. 1 – 3 and by solid lines in FIG. 6. The manner of securing the orthodontic arch wire 99 to the orthodontic bands 88, 90, 92, 94, 96 and 98 and to the other orthodontic bands, not shown, on the remaining teeth, not shown, of the lower jaw 21, and the manner in which that orthodontic arch wire helps reposition those various teeth, are well known to those skilled in the art and are not a part of the present invention.

The numeral 110 denotes an orthodontic band which is secured to one of the molars at the side of the lower jaw 21 which is not shown in FIG. 3; and that molar will peferably be in vertical alignment with the molar 42 of the upper jaw 20. The numeral 112 denotes an orthodontic tube which is shown particularly by FIGS. 3, 4 and 7 and which is welded to the outer surface of the orthodontic band 46 on the tooth 24; and that tube has the axis thereof disposed so it is horizontal and so it is generally parallel to the rear portion of the bone of the upper jaw 20, as shown particularly by FIG. 4. That tube is adjacent to, but is below, a smaller-diameter orthodontic tube 114 which also is welded to the outer surface of the orthodontic band 46. The orthodontic tube 114 accommodates one end of the orthodontic arch wire 65, and that orthodontic tube is not a part of the present invention.

The numeral 116 denotes a large orthodontic tube which is essentially identical to the orthodontic tube 112 and which is welded to the outer surface of the orthodontic band 64 on the tooth 42, as shown by FIG. 4. The orthodontic tube 116 has the axis thereof disposed so it is horizontal and so it is generally parallel to the rear portion of the bone of the upper jaw 20, as shown particularly by FIG. 4. The outer diameters of the orthodontic tubes 112 and 116 are large in comparison with the outer diameter of the orthodontic tube 114, but those outer diameters are relatively small when compared with the vertical dimensions of the orthodontic bands 46 and 64 to which they are welded.

The numeral 118 denotes an orthodontic arch wire which has one end thereof disposed within the orthodontic tube 112, and which has the other end thereof disposed within the orthodontic tube 116. An outwardly-offset portion 119 is provided in that end of the orthodontic arch wire 118 which is held by the orthodontic tube 112; and that outwardly-offset portion is defined by a bend which is immediately adjacent the forward end of that orthodontic tube and by a further bend which is displaced a small fraction of an inch forwardly of that orthodontic tube. As shown particularly by FIG. 4, all portions of the length of the orthodontic arch wire 118 are displaced outwardly of the outer faces of the teeth of the upper jaw 20; but the outwardly-offset portion 119 displaces about one-half of the length of that orthodontic arch wire even further outwardly of those outer faces. However, that outwardly-offset portion will not cause any part of that orthodontic arch wire to chafe or irritate the inner surfaces of the cheeks or lips of the wearer.

The numeral 120 denotes a further orthodontic arch wire which has one end thereof held by the orthodontic tube 112 and which has the other end thereof held by the orthodontic tube 116. The numeral 121 denotes an outwardly-offset portion in that end of the orthodontic arch wire 120 which is held by the orthodontic tube 116; and that outwardly-offset portion is defined by a bend which is immediately adjacent the forward end of the orthodontic tube 116 and by a further bend which is displaced a small fraction of an inch forwardly of that orthodontic tube. As shown particularly by FIG. 4, all portions of the length of the orthodontic arch wire 120 are displaced outwardly of the outer faces of the teeth of the upper jaw 20; but the outwardly-offset portion 121 displaces about one-half of the length of that orthodontic arch wire even further outwardly of those outer faces. However, that outwardly-offset portion will not cause any part of that orthodontic arch wire to chafe or irritate the inner surfaces of the cheeks or lips of the wearer.

The numeral 122 denotes a helical extension spring which is telescoped over the orthodontic arch wire 118; and the un-stressed length of that helical extension spring is considerably less than the effective length of that orthodontic arch wire. The inner diameter of that helical extension spring is sufficiently larger than the diameter of that orthodontic arch wire to permit that helical extension spring to be extended without having any portion thereof bind or jam on that orthodontic arch wire. In addition, the inner diameter of the helical extension spring 122 is large enough to accommodate a short tube 123 which is telescoped over, and which slides freely relative to, the orthodontic arch wire 118. That tube is located at that end of the helical extension spring 122 which is remote from the orthodontic band 64; and that tube has annular grooves 125 adjacent the opposite ends of the exterior thereof. The numeral 126 denotes a helical extension spring which is similar to the helical extension spring 122 but which is telescoped over the orthodontic arch wire 120. The inner diameter of the helical extension spring 126 is sufficiently larger than the diameter of the arch wire 120 to enable that helical extension spring to be extended without having any portion thereof bind or jam on that orthodontic arch wire. Further, the inner diameter of the helical extension spring 126 is large enough to accommodate a short tube, not shown, which is identical to the tube 123; and that tube slides freely relative to, the orthodontic arch wire 120. That tube is located at that end of the helical extension spring 126 which is remote from the orthodontic band 46; and that tube has annular grooves adjacent the opposite ends of the exterior thereof.

The numeral 124 denotes a connecting wire in FIG. 4 which is wound around that end of the helical extension spring 122 which is adjacent the orthodontic tube 116, and which also is wound around the rearwardly-extending end of one or both of the orthodontic arch wires 118 and 120. As shown by FIG. 4, that connecting wire extends from a point forwardly of the orthodontic tube 116 to a point rearwardly of that orthodontic tube. The numeral 128 denotes a further connecting wire which is wound around that end of the helical extension spring 126 which is adjacent the orthodontic tube 112, and which also is wound around the rearwardly-extending end of one or both of the orthodontic arch wires 118 and 120. As shown by FIG. 4, that connecting wire extends from a point forwardly of the orthodontic tube 112 to a point rearwardly of that orthodontic tube.

The ends of the orthodontic arch wires 118 and 120 which are to be telescoped into the orthodontic tube 112 preferably are secured together by a weld; and the other ends of those orthodontic arch wires also are preferably secured together by a weld. Thereafter, the welded ends which are to be held by the orthodontic tube 112 are telescoped through that tube; and then a tie wire 148 is bent around the projecting rear ends of the orthodontic arch wires 118 and 120, the ends of that tie wire are passed forwardly along the exterior of the orthodontic tube 112, one of those ends is passed between the diverging portions of those orthodontic arch wires and is twisted securely to the other end of the tie wire, and the twisted ends of the tie wire are tucked under a portion of the length of the orthodontic arch wire 120. Similarly, after the welded other ends of the orthodontic arch wires 118 and 120 have been telescoped through the orthodontic tube 116, a tie wire, not shown, will be bent around the projecting rear ends of those orthodontic arch wires, the ends of that tie wire will be passed forwardly along the exterior of the orthodontic tube 116, one of those ends will be passed between the diverging portions of those orthodontic arch wires and will be twisted securely to the other end of the tie wire, and the twisted ends of the tie wire will be tucked under a portion of the length of the orthodontic arch wire 118. In this way, the orthodontic arch wires 118 and 120 are fixedly secured to the upper jaw of the wearer.

If, for some reason, an orthodontist did not wish to weld together the ends of the orthodontic arch wires 118 and 120, or did not wish to use a tie wire to secure the ends of those orthodontic arch wires to the orthodontic tube 112, the ends of those orthodontic arch wires could be passed rearwardly through that orthodontic tube, and then one or both of those ends could be bent inwardly to prevent forward movement of those orthdontic arch wires relative to that orthodontic tube. The outwardly-offset portion 119 would prevent rearward movement of the orthodontic arch wires 118 and 120 relative to the orthodontic tube 112. Similarly, if for some reason, an orthodontist did not wish to weld together the ends of the orthodontic arch wires 118 and 120, or did not wish to use a tie wire to secure the ends of those orthodontic arch wires to the orthodontic tube 116, the ends of those orthodontic arch wires could be passed rearwardly through that orthodontic tube, and then one or both of those ends could be bent inwardly to prevent forward movement of those orthodontic arch wires relative to that orthodontic tube. The outwardly-offset portion 121 would prevent rearward movement of the orthodontic arch wires 118 and 120 relative to the orthodontic tube 116.

The diameters of the orthodontic tubes 112 and 116 are sufficiently small, relative to the combined diameters of the welded ends of the orthodontic arch wires 118 and 120, to solidly support those welded ends. In addition, the support which the orthodontic tubes 112 and 116 provide for the welded ends of the orthodontic arch wires 118 and 120 is sufficiently solid to hold all portions of those orthodontic arch wires, which are intermediate those welded ends, fixedly spaced outwardly of the outer faces of the teeth of the upper jaw 20. In this way, the orthodontic arch wires 118 and 120 are fixedly secured to the upper jaw of the wearer in such a way as to permit free movement of the helical extension springs 122 and 126, respectively, relative to them.

The numeral 130 denotes a small-diameter orthodontic tube which is welded to the orthodontic band 110, as shown particularly by FIG. 6. That orthodontic tube holds one end of the orthodontic arch wire 99 that is used to help reposition one or more of the teeth of the lower jaw 21. That orthodontic tube is provided with an outwardly-extending hook 132; and one end of a flexible connector 134 is secured to that hook. That flexible connector is made from a tough non-metallic plastic material; and it is marketed under the trademarks ALASTIC, ELAST-O-CHAIN or POWER CHAIN. The other end of that flexible connector is secured to the free end of the helical extension spring by a connector wire 136, as shown particularly by FIGS. 1 and 4.

The numeral 138 denotes a small-diameter orthodontic tube which is welded to the orthodontic band 88 on the molar 68 of the lower jaw 21 which is in register with the molar 24 of the upper jaw 20. That orhodontic tube supports the other end of the orthodontic arch wire 99; and it has a hook 140 extending outwardly therefrom. A flexible connector 142, which preferably will be identical in nature to the flexible connector 134, has one end thereof secured to the hook 140. The other end of that flexible connector is secured to the free end of the helical extension spring 122 by a connecting wire 144, as shown particularly by FIG. 1, 3 and 4. The flexible connectors 134 and 142 are substantially inextensible; and hence they transmit to the orthodontic bands 110 and 138, without any appreciable diminution, the restorative forces which are developed within the helical extension springs 122 and 126.

The free end of the hook 132, on the orthodontic tube 130, will be bent against that orthodontic tube after the one end of the flexible connector 134 is secured to that hook. Similarly, the free end of the hook 140, on the orthodontic tube 138, will be bent against that orthodontic tube after the one end of the flexible connector 142 is secured to that hook. As a result, accidental separation of those ends of those flexible connectors from those orthodontic tubes will be prevented.

The turns of the connecting wire 144 which engage the helical extension spring 122 will extend into the grooves 125 in the exterior of the small tube 123; and that small tube will enable those turns to be pulled into tight engagement with that helical extension spring without impeding the free movement of that helical extension relative to the orthodontic arch wire 118. Similarly, the turns of the connecting wire 136 which engage the helical extension spring 126 will extend into the grooves in the exterior of the small tube, not shown, which is disposed within the movable end of that helical extension spring; and that small tube will enable those turns to be pulled into tight engagement with that helical extension spring without impeding the free movement of that helical extension spring relative to the orthodontic arch wire 126.

The lengths and diameters of the helical extension springs 122 and 126 and the lengths of the flexible connectors 134 and 142 will preferably be selected to enable each of those helical extension springs to provide a restorative force of between one ounce and three ounces whenever the upper and lower jaws 20 and 21, respectively, are closed. The values of the restorative forces exerted by the helical extension springs can easily be adjusted by adjusting the lengths of the connecting wires 124 and 128. The lengths and diameters of the helical extension springs 122 and 126 will preferably be selected so the restorative forces provided by those helical extension springs will increase from the closed-jaw values of between one and three ounces to open-jaw values of between six and eight ounces when the jaws 20 and 21 are fully open.

The outwardly-offset portion 119 of the orthodontic arch wire 118 displaces the free end of the helical extension spring 122 far enough outwardly of the outer faces of the teeth of the upper jaw 20 to enable all portions of the length of that helical extension spring to experience free and unimpeded movement as the wearer's jaws open and close. Similarly, the outwardly-offset portion 121 of the orthodontic arch wire 120 displaces the free end of the helical extension spring 126 far enough outwardly of the outer faces of the teeth of the upper jaw 20 to enable all portions of the length of that helical extension spring to experience free and unimpeded movement as the wearer's jaws open and close. However, the outwardly-offset portions 119 and 121 are small enough to keep the helical extension springs 122 and 126 from chafing or irritating the inner surfaces of the cheeks or lips of the wearer.

The orthodontic arch wires 118 and 120, the helical extension springs 122 and 126, and the connecting wires 124 and 128 are made from metals which will not irritate any portions of the wearer's mouth, and which will be unaffected by the acidic nature of the wearer's saliva or of any foods eaten by the wearer. One such metal is stainless steel. The orthodontic arch wire 118 and 120 make absolutely certain that no part of either of the helical extension springs 122 and 126 can ever be bitten by the teeth of the wearer; and hence neither of those helical extension springs can be distorted or impaired as the wearer moves his or her jaws. The outwardly-offset portions 119 and 121 of the orthodontic arch wires 118 and 120, respectively, minimize the likelihood that the flexible connectors 134 and 142 will move into position between the upper and lower teeth of the wearer as the wearer opens and closes his jaws. However, because those flexible connectors are made of tough material, they will not be severed even if repeatedly bitten by the teeth of the wearer. Because those flexible connectors are made of non-metallic material, they will not cause breaking or chipping of any teeth of the wearer, even if the wearer were to bite hard on either or both of those flexible connectors.

The repositioning forces which the helical extension springs 122 and 126 develop between the upper and lower jaws 20 and 21, respectively, of the wearer will tend to shift the lower jaw forwardly relative to the upper jaw. If it ever became desirable for the upper jaw of a person to be shifted forwardly relative to the lower jaw of that person, the orthodontic arch wires 118 and 120 would be secured to the lower jaw, and the rear ends of the flexible connectors 134 and 142 would be connected to the upper jaw.

When two orthodontic arch wires, two helical extension springs, and two flexible connectors are used, the resulting forwardly-directed forces will tend to cause both sides of the spring-equipped jaw to move forwardly. If it became desirable to apply forwardly-directed forces to just one side of a jaw, only one orthodontic arch wire, one helical extension spring, and one flexible connector would be needed.

The drawing shows the orthodontic arch wires 65 and 99 being used at the same time the orthodontic arch wires 118 and 120, the helical extension springs 122 and 126, and the flexible connectors 134 and 142 are used. This has been done because persons who have mal-occlusions usually require re-positioning of their teeth. However, in the event a person had a mal-occlusion but did not require re-positioning of the teeth in either the upper or lower jaw, either or both of the orthodontic arch wires 65 and 99 could be eliminated. In such event the orthodontic bands that are used to support the portions of those orthodontic arch wires which are intermediate the ends of those orthodontic arch wires also could be eliminated. Further, the orthodontic tube 114 and its counterpart could be eliminated. However, the orthodontic tubes 130 and 138, or some hooks, would still be required; because the hooks 132 and 140, respectively, are needed to hold the rear ends of the flexible connectors 134 and 142.

The helical extension springs 122 and 126 preferably have unstressed inner diameters of between fifty-five thousandths and sixty-five thousandths of an inch. Also, each of those helical extension springs preferably is made from wire having a diameter of between eight thousandths and twelve thousands of an inch. The diameter of each of the orthodontic arch wires 118 and 120 is thirty-five thousandths of an inch. The inner diameter of each of the orthodontic tubes 112 and 114 preferably is fifty-one thousandths of an inch; and the inner diameters of orthodontic tube 114 and of its counterpart are even smaller. The outwardly-offset portions 119 and 121, respectively, of the orthodontic arch wires 118 and 120 are hard and stiff; but the rear ends of those orthodontic arch wires are annealed to make them readily bendable by an orthodontist.

Although the drawings and accompanying description have shown and described a preferred embodiment of the present invention it should be apparent to those skilled in the art that various changes may be made in the form of the invention without affecting the scope thereof.

What I claim is:

1. An orthodontic appliance for applying a repositioning force between teeth of a person's jaws to improve the occlusion of those jaws which comprises an orthodontic arch wire that is securable to one of said jaws, said orthodontic arch wire being located exteriorly one of the outer faces of the teeth of said one jaw and being bowed to generally follow the curvature of said one jaw, a helical extension spring that is telescoped over, and hence is supported and guided by, a portion of the length of said orthodontic arch wire, means to limit movement of one end of said helical extension spring relative to one end of said orthodontic arch wire while permitting the other end of said helical extension spring to move relative to the other end of said orthodontic arch wire, said helical extension spring having an inner diameter which is sufficiently larger than the diameter of said orthodontic arch wire to permit said other end of said helical extension spring to move freely relative to said other end of said orthodontic arch wire even though said orthodontic arch wire is bowed to generally follow the curvature of said one jaw, said other end of said helical extension spring occupying a predetermined position along the length of said orthodontic arch wire whenever said helical extension spring is in its unstressed condition, and a flexible connector which connects said other end of said helical extension spring to the other of said jaws at a point which is displaced along the length of said orthodontic arch wire from said predetermined position which said other end of said helical extension spring occupies whenever said helical extension spring is in its unstressed condition, said flexible connector and said helical extension spring being dimensioned to apply repositioning forces to said teeth and hence to said jaws.

2. An orthodontic appliance as claimed in claim 1 wherein said flexible connector is substantially inextensible, whereby substantially all of said repositioning force is developed by the extension of said helical extension spring.

3. An orthodontic appliance as claimed in claim 1 wherein said other end of said orthodontic arch wire is displaced from said outer faces of the teeth of said one jaw a greater distance than said one of said orthodontic arch wire is displaced from said outer faces of the teeth of said one jaw, whereby said other end of said helical extension spring is able to move freely relative to said teeth as well as to move freely relative to said other end of said orthodontic arch wire.

4. An orthodontic appliance as claimed in claim 1 wherein said one end of said helical extension spring is located at one side of said one jaw, and wherein the portion of said helical extension spring which is intermediate said one and said other ends of said helical extension spring extends around the front of said one jaw whenever said helical extension spring is in its stressed condition, whereby said other end of said helical extension spring is at the opposite side of said one jaw whenever said helical extension spring is in its stressed condition.

5. An orthodontic appliance as claimed in claim 1 wherein said one end of said orthodontic arch wire is secured to said one jaw, and wherein said other end of said orthodontic arch wire is secured to said one jaw, but wherein the intervening portion of said orthodontic arch wire is spaced from said one jaw.

6. An orthodontic appliance as claimed in claim 1 wherein said helical extension spring is in stressed condition whenever said jaws are closed and thereby provides a predetermined repositioning force, and wherein said helical extension spring is in a condition of greater stress whenever said jaws are open and thereby provides a greater repositioning force.

7. An othodontic appliance as claimed in claim 1 wherein a second orthodontic arch wire has an end thereof securable to said one jaw adjacent said other end of the first said orthodontic arch wire and has the opposite end thereof securable to said one jaw adjacent said one end of said first said orthodontic arch wire, wherein said second orthodontic arch wire is located exteriorly of said teeth of said one jaw and is bowed to generally follow said curvature of said one jaw, wherein a second helical extension spring is telescoped over, and hence is supported and guided by, a portion of the length of said second orthodontic arch wire, wherein second means limits movement of one end of said second helical extension spring relative to one end of said second orthodontic arch wire while permitting the other end of said second helical extension spring to move relative to the other end of said second orthodontic arch wire, wherein said second helical extension spring has an inner diameter which is sufficiently larger than the diameter of said second orthodontic arch wire to permit said other end of said second helical extension spring to move freely relative to said other end of said second orthodontic arch wire even though said second orthodontic arch wire is bowed to generally follow the curvature of said one jaw, wherein said other end of said second helical extension spring occupies a second predetermined position along the length of said orthodontic arch wire whenever said second helical extension spring is in its unstressed condition, wherein a second flexible connector connects said other end of said second helical extension spring to said other of said jaws at a point which is displaced along the length of said second orthodontic arch wire from said predetermined position which said other end of said second helical extension spring occupies whenever said second helical extension spring is in its unstressed condition, wherein said second flexible connector and said second helical extension spring are dimensioned to apply repositioning forces to said teeth and hence to said jaws, and wherein the first said and said second orthodontic wires are adjacent to each other but are displaced far enough apart to permit said other end of the first said helical extension spring to move freely without engaging any part of said second helical extension spring and to permit said other end of said second helical extension spring to move freely without engaging any part of said first said helical extension spring.

8. An orthodontic appliance for applying a repositioning force between teeth of a person's jaws to improve the occlusion of those jaws which comprises an orthodontic arch wire that is securable to one of said jaws, said orthodontic arch wire being located exteriorly of the outer faces of the teeth of said one jaw, a helical extension spring that is telescoped over, and hence is supported and guided by, a portion of the length of said orthodontic arch wire, means to limit movement of one end of said helical extension spring relative to one end of said orthodontic arch wire while permitting the other end of said helical extension spring to move relative to the other end of said orthodontic arch wire, said helical extension spring having an inner diameter which is sufficiently larger than the diameter of said orthodontic arch wire to permit said other end of said helical extension spring to move freely relative to said other end of said orthodontic arch wire, said other end of said helical extension spring occupying a predetermined position along the length of said orthodontic arch wire whenever said helical extension spring is in its unstressed condition, and a flexible connector which connects said other end of said helical extension spring to the other of said jaws at a point which is displaced along the length of said orthodontic arch wire from said predetermined position which said other end of said helical extension spring occupies whenever said helical extension spring is in its unstressed condition, said flexible connector and said helical extension spring being dimensioned to apply repositioning forces to said teeth and hence to said jaws.

9. An orthodontic appliance for applying a repositioning force between teeth of a person's jaws to improve the occlusion of those jaws which comprises a wire that is securable to one of said jaws, said wire being located exteriorly of the outer faces of the teeth of said one jaw, a helical extension spring that is telescoped over, and hence is supported and guided by, a portion of the length of said wire, means to limit movement of one end of said helical extension spring relative to one end of said wire while permitting the other end of said helical extension spring to move relative to the other end of said wire, said helical extension spring having an inner diameter which is sufficiently larger than the diameter of said wire to permit said other end of said helical extension spring to move freely relative to said other end of said wire, and a flexible connector which connects said other end of said helical extension spring to the other of said jaws, said flexible connector and said helical extension spring being dimensioned to apply repositioning forces to said teeth and hence to said jaws.

10. An orthodontic appliance as claimed in claim 9 wherein the securement between said wire and said one jaw is adjacent said ends of said wire, whereby the portions of said wire which are intermediate said ends of said wire will not obstruct extension and retraction of said helical extension spring.

11. An orthodontic appliance as claimed in claim 9 wherein said wire is bowed to have a curvature generally similar to that of said one jaw but wherein said wire has an outwardly-offset portion adjacent one end thereof.

12. An orthodontic appliance as claimed in claim 9 wherein a second wire has one end thereof securable to said one jaw adjacent said other end of the first said wire and has the other end thereof securable to said one jaw adjacent said one end of first said wire, wherein said second wire is located exteriorly of said outer faces of said teeth of said one jaw, wherein a second helical extension spring is telescoped over, and hence is supported and guided by, a portion of the length of said second wire, wherein second means limits movement of one end of said second helical extension spring relative to an end of said second wire while permitting the other end of said second helical extension spring to move relative to the opposite end of said second wire, wherein said second helical extension spring has an inner diameter which is sufficiently larger than the diameter of said second wire to permit said other end of said second helical extension spring to move freely relative to said opposite end of said wire, wherein a second flexible connector connects said other end of said second helical extension spring to said other of said jaws, wherein said second flexible connector and said second helical extension spring are dimensioned to apply repositioning forces to said teeth and hence to said jaws, wherein an orthodontic tube is securable to one tooth of said one jaw, wherein a second orthodontic tube is securable to another tooth of said one jaw, and wherein said ends of said wires are disposable within said orthodontic tubes.

13. An orthodontic appliance as claimed in claim 9 wherein a tube is disposed within said other end of said helical extension spring and is telescoped over, and is freely movable relative to, said wire, 14. An orthodontic appliance as claimed in claim 9 wherein a tube is disposed within said other end of said helical extension spring and is telescoped over, and is freely movable relative to, said wire, and wherein said tube has a change of surface at the exterior thereof to enable a connecting element to tightly secure, said other end of said helical extension spring to said tube.

* * * * *